(12) United States Patent
Buhring et al.

(10) Patent No.: US 9,580,686 B2
(45) Date of Patent: Feb. 28, 2017

(54) MSC SURFACE MARKER

(71) Applicant: Eberhard-Karls-Universitaet Tuebingen Universitaetsklinikum, Tuebingen (DE)

(72) Inventors: Hans-Jorg Buhring, Tubingen (DE); Sabrina Grimm, Rottenburg a.N. (DE); Flavianna Cerabona, Bissingen (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 80 days.

(21) Appl. No.: 14/493,160

(22) Filed: Sep. 22, 2014

(65) Prior Publication Data

US 2015/0010516 A1    Jan. 8, 2015

Related U.S. Application Data

(63) Continuation of application No. PCT/EP2013/056033, filed on Mar. 22, 2013.

(30) Foreign Application Priority Data

Mar. 23, 2012 (DE) .................. 10 2012 102 532

(51) Int. Cl.
| | |
|---|---|
| *A61K 38/00* | (2006.01) |
| *C12N 5/00* | (2006.01) |
| *C12N 5/0775* | (2010.01) |
| *C07K 16/28* | (2006.01) |
| *C07K 16/40* | (2006.01) |
| *G01N 33/569* | (2006.01) |
| *A61K 35/28* | (2015.01) |
| *A61K 39/00* | (2006.01) |
| *A61K 35/12* | (2015.01) |

(52) U.S. Cl.
CPC ............ *C12N 5/0663* (2013.01); *A61K 35/28* (2013.01); *C07K 16/28* (2013.01); *C07K 16/2803* (2013.01); *C07K 16/2863* (2013.01); *C07K 16/40* (2013.01); *G01N 33/56966* (2013.01); *A61K 2035/124* (2013.01); *A61K 2039/507* (2013.01); *G01N 2333/705* (2013.01); *G01N 2333/70503* (2013.01); *G01N 2333/71* (2013.01); *G01N 2333/916* (2013.01)

(58) Field of Classification Search
None
See application file for complete search history.

(56) References Cited

U.S. PATENT DOCUMENTS

8,163,495 B2    4/2012 Buhring et al.

FOREIGN PATENT DOCUMENTS

| DE | 10 2006 043 625 A1 | 3/2008 |
|---|---|---|
| ES | 2 370 794 A1 | 12/2011 |

OTHER PUBLICATIONS

Bühring et al., "Phenotypic Characterization of Distinct Human Bone Marrow-Derived MSC Subsets," *Annals of the New York Academy of Sciences*, 1176(1): 124-134 (Sep. 1, 2009).

English Language Translation of International Preliminary Report on Patentability and Written Opinion from PCT/EP2013/056033, 7 pages, (mailed Oct. 16, 2014).

Köehler and Milstein, "Continuous Cultures of Fused Cells Secreting Antibody of Predefined Specificity;" *Nature* 256:495-497 (Aug. 7, 1975).

Sharon et al., Expression of a $V_H C_K$ Chimaeric Protein in Mouse Myeloma Cells; *Nature* 309: 364-367 (1984).

*Primary Examiner* — Michail Belyavskyi
(74) *Attorney, Agent, or Firm* — Klarquist Sparkman, LLP

(57) ABSTRACT

The present invention relates to the use of at least one antibody which binds to the SUSD2 antigen, or to functional fragments of the antibody, in combination with at least one of the following: an antibody which binds to CD140b, an antibody which binds to CD56, and/or an antibody which binds to TNAP, or functional fragments thereof, for isolation of mesenchymal stem cells, especially those having particularly chondrocytic and osteogenic differentiation potential. The invention further relates to processes for isolating such stem cells using these antibodies.

9 Claims, 4 Drawing Sheets

MSC SURFACE MARKER

CROSS REFERENCE TO RELATED APPLICATIONS

This application is a continuation of international patent application PCT/EP2013/056033, filed on Mar. 22, 2013, designating the U.S., which international patent application has been published in German language and claims priority from German patent application DE 10 2012 102 532.0, filed on Mar. 23, 2012. The entire contents of these priority applications are incorporated herein by reference.

BACKGROUND OF THE INVENTION

The present invention relates to the isolation and/or identification of highly pure mesenchymal stem cells by means of a novel cell surface marker, and the use of this cell surface marker and the isolated stem cells.

Mesenchymal stem cells (MSC), also called mesenchymal stromal cells, are pluripotent cells which possess the ability, under suitable in vitro and in vivo conditions, to differentiate into various mesenchymal tissues. Thus they can for example differentiate into osteocytes, chondrocytes, adipocytes and myocytes, and form bone, cartilage, adipose and muscle tissue. In addition, however, they can also differentiate into astrocytes, neurons, endothelial cells, hepatocytes, pancreas-like cells and pulmonary epithelial cells. Morphologically, they can be recognized by their fibroblastoid phenotype, and can be found in various human adult and embryonic tissues, including the brain, bone marrow, umbilical blood, in blood vessels, in the skeletal muscle, skin, liver, gums and the placenta.

MSC from bone marrow express a range of surface markers such as for example CD105 (endoglin, SH2), CD73 (ecto-5'-nucleotidase, SH3, SH4), CD166 (ALCAM), CD29 ($\beta$1-integrin), CD44 (H-CAM) and CD90 (Thy-1), which are to some extent also found on endothelial and epithelial cells and on muscle cells. However, MSC can be distinguished from hematopoietic stem cells since MSC do not express the markers CD45, CD34 and CD133 specific for hematopoietic stem cells.

MSC have the property of rapidly and stably adhering on plastic or glass surfaces and forming fibroblast colonies ("colony-forming units fibroblast" (CFU-F)). However, the latter are heterogenous as regards their proliferation and differentiation capabilities.

MSC with a defined differentiation potential are of great interest in medicine and research. They can in particular be obtained from the bone marrow, even from that of older people, have a high division rate and can as stated differentiate into tissue cells of mesenchymal origin. They could therefore be used directly for example in the context of stem cell therapies for the treatment of degenerative diseases of organs such as bone, cartilage, tendons, muscle, connective tissue, blood cells, etc.

For the obtention or isolation of MSC, unfractionated bone marrow cells are at present used as the starting material. In culture bottles, as well as MSC, other cells such as macrophages and endothelial cells also adhere. After defined periods, the non-adhering cells (mostly hematopoietic cells) from the sample are discarded. However the cells obtained in this manner are poorly defined and differentiate not only into heterogenous MSC populations, but also into osteoblasts and/or into osteoblast precursor cells, adipose cells, reticular cells, macrophages and endothelial cells. Hence specific treatment of degenerative diseases of an organ with MSC with no defined differentiation potential is difficult, or problematic because of possible side effects.

Hitherto, the isolation of especially pure MSC, both from primary tissue and also from cultured MSC was not possible or known according to the prior state of the art, but would offer the advantage of specifically using stem cells thus identified for the therapy/treatment of diseased, degenerated or damaged tissue into which the stem cells thus specifically isolated differentiate.

Thus for example cartilage injuries could be treated by introducing specifically isolated mesenchymal stem cells with chondrogenic differentiation potential either directly in situ into the affected tissue, where they differentiate into chondrocytes and thereby replace the damaged tissue (stem cell therapy). On the other hand, however, differentiation into chondrocytes in vitro can also be of interest if differentiated chondrocytes are to be isolated, for example for research/diagnosis/medicine.

Against this background, an object of the present invention is to provide novel ways whereby especially pure mesenchymal stem cell populations can be isolated.

SUMMARY OF THE INVENTION

According to the invention, this and other problems is/are solved by the use of at least one monoclonal antibody which binds to the cell surface marker SUSD2 ("Sushi domain containing protein 2"), or to functional fragments of the antibody which bind to the cell surface marker SUSD2, in combination with at least one second antibody which binds to CD140b (PDGF-RB =platelet derived growth factor receptor beta), TNAP ("tissue non-specific alkaline phosphatase") and/or CD56, or functional fragments of the antibody in a method for identifying/isolating mesenchymal stem cells, particularly mesnenchymal stem cells with chondrogenic differentiation potential. Through the combined use of these at least two antibodies, the signal strength in the labeling is increased, as a result of which more effective purification can be achieved during selection.

The problems are further solved by a method for the isolation and/or identification of MSC wherein the antibodies binding to SUSD2 and those binding to CD140b, TNAP and/or CD56 are used.

The invention further relates to the stem cells isolated in this manner and the use thereof, in particular in therapy.

In their own experiments, the inventors of the present application were able to show that with use of the stated antibodies it is possible to isolate particularly pure MSCs. These can then, under suitable in vivo or in vitro conditions, differentiate or be differentiated into chondrocytes, osteoblasts and adipocytes.

Thereby for the first time a tool is provided with which highly pure MSC populations can be obtained. This was not previously possible in the state of the art.

In particular, by means of the newly identified surface marker SUSD2, a tool is provided with which for the first time, in combination with CD140b, CD56 and/or TNAP, MSC which represent a particularly pure MSC subpopulation can be specifically identified.

SUSD2 is an integral membrane protein comprising 822 amino acids which has so far been detected in the organs tonsils, lung, intestine and kidneys. Its sequence and further information are to be found in the UniProt database (www.uniprot.org) under the entry Q9UGT4, to which reference is herewith explicitly made. A connection with the expression of this membrane protein on mesenchymal stem cells had not previously been described in the state of the art.

Hence on the basis of the novel use and the novel method, MSC can be provided which for example can in turn advantageously be used in therapy and prophylaxis or else in diagnostics and research. Thus the stem cells isolated in this way can in particular be used, for example in the context of stem therapy, for the treatment of diseases which are characterized by degenerated, injured or damaged tissue. For this, the stem cells isolated by means of the method according to the invention are transplanted into the tissue affected (for example also in combination with certain implants), and there differentiate into the relevant tissue. The degenerated tissue is thereby regenerated and becomes functional again.

By means of the novel use and methods, the mesenchymal stem cells can be isolated highly pure and identified, both from primary tissues and also from cultured cells.

Thus according to the invention anti-SUSD2 antibodies can be used in combination with anti-CD140b antibodies, anti-TNAP antibodies and/or anti-CD56 antibodies.

According to one aspect of the invention, the at least one antibody binding to SUSD2 is selected from:
the antibodies W5C5 or W3D5 or a mixture of both these antibodies, which are each produced by hybridoma cells which in accordance with the Budapest Treaty were each deposited on 21 Feb. 2007 at the German Collection for Cell Cultures and Microorganisms under the deposition numbers DSM ACC2813 (W5C5) and DSM ACC2815 (W3D5)
functional fragments of the antibody W5C5 or W3D5 which are still capable of binding respectively to the same epitope as the complete antibodies W5C5 and W3D5, and
monoclonal antibodies which respectively bind to the same epitope as the antibodies W5C5 or W3D5.

In particular, it is preferred if the antibody W5C5 and/or the antibody W3D5 is used. The two antibodies W5C5 or W3D5 are produced, respectively, by hybridoma cell lines which in accordance with the Budapest Treaty were each deposited on 21 Feb. 2007 at the German Collection for Cell Cultures and Microorganisms, Inhoffenstr. 7B, D-38125, Braunschweig, GERMANY under the deposition numbers DSM ACC2813 (W5C5) and DSM ACC2815 (W3D5); prolongation of the deposition has been requested. Functional or binding-relevant fragments of these antibodies can also advantageously be used. There and herein, "binding-relevant" or "functional" fragments of the antibodies are understood to be any fragment of the antibodies, or a sequence derived therefrom, which is still capable of binding to the same epitope as the complete antibodies.

The antibodies W5C5 or W3D5 bind to different epitopes of SUSD2; although these antibodies are available in the state of the art, the antigen to which these antibodies bind was previously unknown.

According to another aspect of the invention, the anti-CD140b antibody is selected from the group:
the antibody 28D4,
functional fragments of the antibody 28D4, and
an antibody which binds to the same epitope as the antibody 28D4.

Various anti-CD140b antibodies are known and are for example obtainable from GenWay Biotec, San Diego, USA, RayBiotech Inc., Norcross, USA, AbD Serotec, Raleigh, USA, BD Biosciences, San Jose, USA, Millipore Upstate Biotechnology, USA, Biolegend, San Diego, USA, etc.

The CD140b-specific antibody 28D4 is for example obtainable from the firm BD Biosciences, USA, and has proved useful in other studies as a marker for MSC. However, it was not previously known that highly pure subpopulations of mesenchymal stem cells can be obtained with a combination of antibodies which are directed against SUSD2 and CD140B.

According to another aspect of the invention the anti-TNAP antibody is selected from the group:
the antibody W8B2 which is produced by the cell line deposited at the German Collection of Microorganisms and Cell Cultures, Inhoffenstr. 7B, D-38125, Braunschweig, GERMANY, with the No. ACC2567,
functional fragments of the antibody W8B2 which is produced by the cell line deposited at the German Collection of Microorganisms and Cell Cultures with the No. ACC2567, and
an antibody which binds to the same antigen or epitope as the antibody W8B2.

The TNAP-specific antibody W8B2 has proved useful in other studies as a marker for MSC. However, it was not previously known that highly pure subpopulations of mesenchymal stem cells can be obtained with a combination of antibodies which are directed against SUSD2 and TNAP. In accordance with the Budapest Treaty, the cells producing the antibody W8B2 were deposited at the German Collection for Cell Cultures and Microorganisms (DSMZ) on 14 Aug. 2002, at which time prolongation of their deposition was secured.

According to another aspect, the antibody binding to CD56 is selected from the group:
the antibody 39D5 which is produced by the cell line deposited at the German Collection of Microorganisms and Cell Cultures, Inhoffenstr. 7B, D-38125, Braunschweig, GERMANY, with the No. DSM ACC 2930,
functional fragments of the antibody 39D5 which is produced by the cell line deposited at the Gelman Collection of Microorganisms and Cell Cultures with the No. DSM ACC 2930, and
an antibody which binds to the same epitope as the antibody 39D5 which is produced by the cell line deposited at the German Collection of Microorganisms and Cell Cultures with the No. DSM ACC 2930.

In one embodiment of the use or method according to the invention, in addition to the combination of an anti-SUSD2 and an antibody directed against CD140b, CD56 and/or TNAP, an antibody or functional fragments thereof, directed against CD271 is also used.

Herein, as already mentioned above, the term "functional fragments" as used in the application is intended to mean substances which are parts/segments of the disclosed antibodies and which still display and possess the functional properties, in particular the cell binding properties, of the antibodies from which they are derived. Also, these fragments can be used either as such or else in combination with other fragments; in the context of the present invention, the latter should also be understood to mean modified W5C5, W3D5, W8B2, 39D5 and 28D4 antibodies which have been adapted, for example humanized, for appropriate uses and applications in man.

Thus according to the invention the following combinations can be used for the isolation/identification of highly pure MSC: W5C5 and/or W3D5 with anti-CD140b antibodies, in particular 28D4; W5C5 and/or W3D5 with anti-CD56 antibodies, in particular 39D5; W5C5 and/or W3D5 with anti-TNAP antibodies, in particular W8B2; W5C5 and/or W3D5 with anti-CD140b antibodies, in particular 28D4, and with anti-CD56 antibodies or anti-TNAP antibodies, W5C5 and/or W3D5 with anti-CD56 antibodies, in particular 39D5, and with anti-CD140b antibodies, in particular 28D4 or anti-TNAP antibodies, in particular W8B2; W5C5 and/or W3D5 with anti-TNAP antibodies, in particular W8B2; and with anti-CD140b antibodies, in particular 28D4 or anti-CD56 antibodies, in particular 39D5; or W5C5 and/or W3D5 with anti-CD140b antibodies, in particular 28D4, anti-CD56 antibodies, in particular 39D5 and anti-TNAP antibodies, in particular W8B2.

The antibodies suitable for the purposes of the present invention are monoclonal, and other antibodies directed against SUSD2, CD140b, TNAP or CD56 can be obtained using the antibodies W5C5 and W3D5, 28D4, W8B2 and 39D5. An introduction to the obtention of monoclonal antibodies was published by Köhler and Milstein ("Continuous cultures of fused cells secreting antibody of defined specificity", Nature, (1975), 256: 495-497).

Herein, however, fragments of such antibodies such as for example Fab, F(ab)'$_2$ of scFv fragments, and other fragments such as CDR ("complementarity-determining region"), hypervariable region) are also referred to as antibodies in the sense and context of the present invention, so long as they possess their functionality, i.e. the specific binding properties like the "whole" antibodies from which they are derived. Such antibody fragments can for example also be produced recombinantly with the use of methods known in the state of the art.

Hence it also goes without saying that the antibodies W5C5 and W3D5 and 28D4 can also be appropriately humanized, and in the context of the invention disclosed here can be used for the applications and/or methods according to the invention, in particular also for stem cell therapy.

Humanized antibodies can for example be chimeric antibodies in which the constant regions of the animal antibodies (for example of mouse or rabbit antibodies) have been replaced by the corresponding regions of human antibodies, for example the Fc fragment (Sharon et al., Nature, (1984), 309: 364-367). Alternatively, the CDR of the animal antibodies can also be linked with human antibodies, this process is called antibody "reshaping". In a further different process, human antibodies are produced in transgenic animals.

Further, in one application according to the invention, the antibodies, for example in humanized form, or functional fragments thereof, can be applied or introduced onto appropriate implantable medical devices, and be implanted together with the device into the patient to be treated at the sites/tissue defects to be treated. At the sites to be treated, mesenchymal stem cells are then recruited via the antibodies, and attach themselves on the implant, differentiate and thus form new tissue. Suitable medical devices here are any biocompatible implants, endoprostheses, for example stents, of any kind, which are introduced into the patient either permanently or temporarily. The devices can optionally also consist of completely or partly absorbable materials and as well as the antibodies contain further therapeutic active substances which are normally used in implants/transplants to be introduced into a body.

As already mentioned above, the present invention also relates to a method for the isolation and/or identification of mesenchymal stem cells which comprises the following steps:
a) contacting a sample which contains mesenchymal stem cells with at least one antibody which binds to antigen SUSD2, or with functional fragments of the antibody,
b) optionally contacting a sample which contains mesenchymal stem cells with a further antibody which binds to the antigen SUSD2, or with functional fragments of the antibody,
c) contacting the sample with at least one antibody which binds to CD140b, CD56, TNAP and/or CD271, or with functional fragments of the antibody, and/or
d) isolation and/or identification of cells to which i) the at least one antibody or fragments thereof which binds to the antigen SUSD2, and ii) the at least one antibody which binds to CD140b, CD56, TNAP and/or CD271 has bound.

With this embodiment of the method according to the invention, highly pure mesenchymal stem cells can be identified and/or isolated, and in particular those which possess a chondrogenic differentiation potential. The stem cells thus obtained can then be used either directly in the context of stem cell therapy (autologous or allogenic therapy), where they differentiate in situ into chondrocytes and can thus regenerate degenerated or damaged cartilage tissue.

On the other hand, the MSC obtained with the method according to the invention can also first be differentiated in vitro into chondrocytes, and then be used for the treatment of diseased or degenerated tissue.

Particularly in recent years, autologous chondrocyte transplantation has developed into a preferred intervention for the treatment of (articular) cartilage defects of vertebral disk and knee, in which the hyaline cartilage has to be restored. For this, samples are taken from the patient from an undamaged joint area by an arthroscopy, and the cartilage cells contained therein grown in the laboratory on special matrices. The tissue arising thereby, namely the new cartilage, is then transplanted into the diseased/degenerated joint by a tissue-conserving second operation.

With the method according to the invention, it is now for the first time possible specifically to isolate stem cells with for example chondrogenic differentiation potential from the tissue of a patient and to obtain rapid, efficient and specific culturing of chondrocyte tissue for subsequent transplantation into the sample donor (autologous transplantation) or another recipient (allogenic transplantation).

According to one aspect of the method according to the invention the anti-SUSD2 antibody is selected from the group:
the antibodies W5C5 or W3D5 or from a mixture of these antibodies, which are each produced by hybridoma cells which in accordance with the Budapest Treaty were each deposited on 21 Feb. 2007 at the German Collection for Cell Cultures and Microorganisms under the deposition numbers DSM ACC2813 (W5C5) and DSM ACC2815 (W3D5)
functional fragments of the antibody W5C5 or W3D5 which are still capable of binding respectively to the same epitope as the complete antibodies W5C5 and W3D5, and
monoclonal antibodies which respectively bind to the same epitope as the antibodies W5C5 or W3D5.

Further, according to one aspect of the method according to the invention, the anti-CD140b antibody is selected from the group:
the antibody 28D4,
functional fragments of the antibody 28D4, and
antibodies which bind to the same epitope as the antibody 28D4.

Further, in a further aspect of the method according to the invention, the antibody binding to CD56 is selected from the group:

the antibody 39D5 which is produced by the hybridoma cell line deposited at the German Collection of Microorganisms and Cell Cultures with the No. DSM ACC 2930, functional fragments of the antibody 39D5, and antibodies which bind to the same epitope as the antibody 39D5 which is produced by the hybridoma cell line deposited at the German Collection of Microorganisms and Cell Cultures.

As explained above for the use according to the invention, one or more anti-SUSD2 antibodies can be used in the method according to the invention, in particular the antibodies W5C5 and W3D5 or a combination of both these antibodies, in combination with either anti-140b antibodies, anti-CD56 antibodies or anti-TNAP antibodies, or in combination with a mixture of anti-140b antibodies, anti-CD56 antibodies and anti-TNAP antibodies, wherein the antibodies 28D4 (CD140b), 39D5 (CD56) and W8B2 (TNAP) are preferred.

The inventors have established in their own experiments that using the antibodies W5C5 and/or W3D5 in a method for the isolation/identification of mesenchymal stem cells, a specific enrichment of highly pure mesenchymal stem cells could be obtained.

The present invention further relates to the use of stem cells which have been isolated/identified with the method according to the invention for therapy, diagnostics or research.

Also, in one embodiment it is preferred if the stem cells obtained with the method according to the invention are used for the defined generation of chondrocytes, namely in vivo or in vitro.

Further, in a further aspect of the invention, the stem cells isolated and/or identified with the method according to the invention which have been differentiated into chondrocytes, are used for the therapy and/or prophylaxis of degenerated or susceptible tissue.

In particular, the stem cells obtained with the method according to the invention are used for the therapy and/or prophylaxis of cartilage damage and/or bone damage, degeneration or diseases, in particular of the knee and vertebral disks, or for rheumatoid arthritis. Rheumatoid arthritis is an autoimmune disease and in this disease also the use of stem cells for tissue replacement (i.e. for so-called "tissue repair") can be of use.

According to the invention, therefore, a pharmaceutical composition is also provided, as well as a kit, which contains a combination of at least one of the antibodies W5C5 or W3D5 or both of these antibodies, with the antibody 28D4 or W8B2 or 39D5.

Further, the invention relates to a pharmaceutical composition containing stem cells which have been isolated/identified according to the method according to the invention, as well as at least one pharmaceutically acceptable carrier and/or auxiliary substance, and optionally therapeutically active substances.

Herein, "pharmaceutically acceptable carrier or auxiliary substances" is understood to mean any substance/composition to be administered to a patient in the pharmacy in connection with, which does not adversely influence the activity of the cells/antibodies, and/or can pharmacologically support or facilitate the use of the pharmaceutical composition.

Herein, "therapeutically active substance" is understood to mean any substance which is used for the purposes of a treatment or amelioration of a clinical picture of a patient.

The pharmaceutical compositions can be administered systemically, i.e. for example orally, subcutaneously, intravenously, rectally, parenterally, intramuscularly, intraperitoneally, transdermally or topically, wherein the type of administration will depend on the nature of the disease, the clinical picture, and the condition of the patient. Likewise, the administration can take place repeatedly or once time, wherein the administration in the first case can take place once or several times per day and/or over a longer period.

In addition to the active substances, the pharmaceutical composition can also contain buffers, diluents and/or additives. Suitable buffers include for example Tris HCl, glycine and phosphate, and suitable diluents for example aqueous NaCl solutions, lactose or mannitol. Suitable additives include for example detergents, solvents, antioxidants and preservatives. An overview of such additional ingredients can be found for example in A. Kibbe: "Handbook of Pharmaceutical Excipients", $3^{rd}$ Ed., 2000, American Pharmaceutical Association and Pharmaceutical Press.

It goes without saying that the features mentioned above and those still to be explained below can be used not only in the combination stated in each case, but also in other combinations or alone, without departing from the scope of the present invention.

BRIEF DESCRIPTION OF THE DRAWINGS

The invention is explained in more detail in the description below and the appended diagrams. In these.

Figure 1:
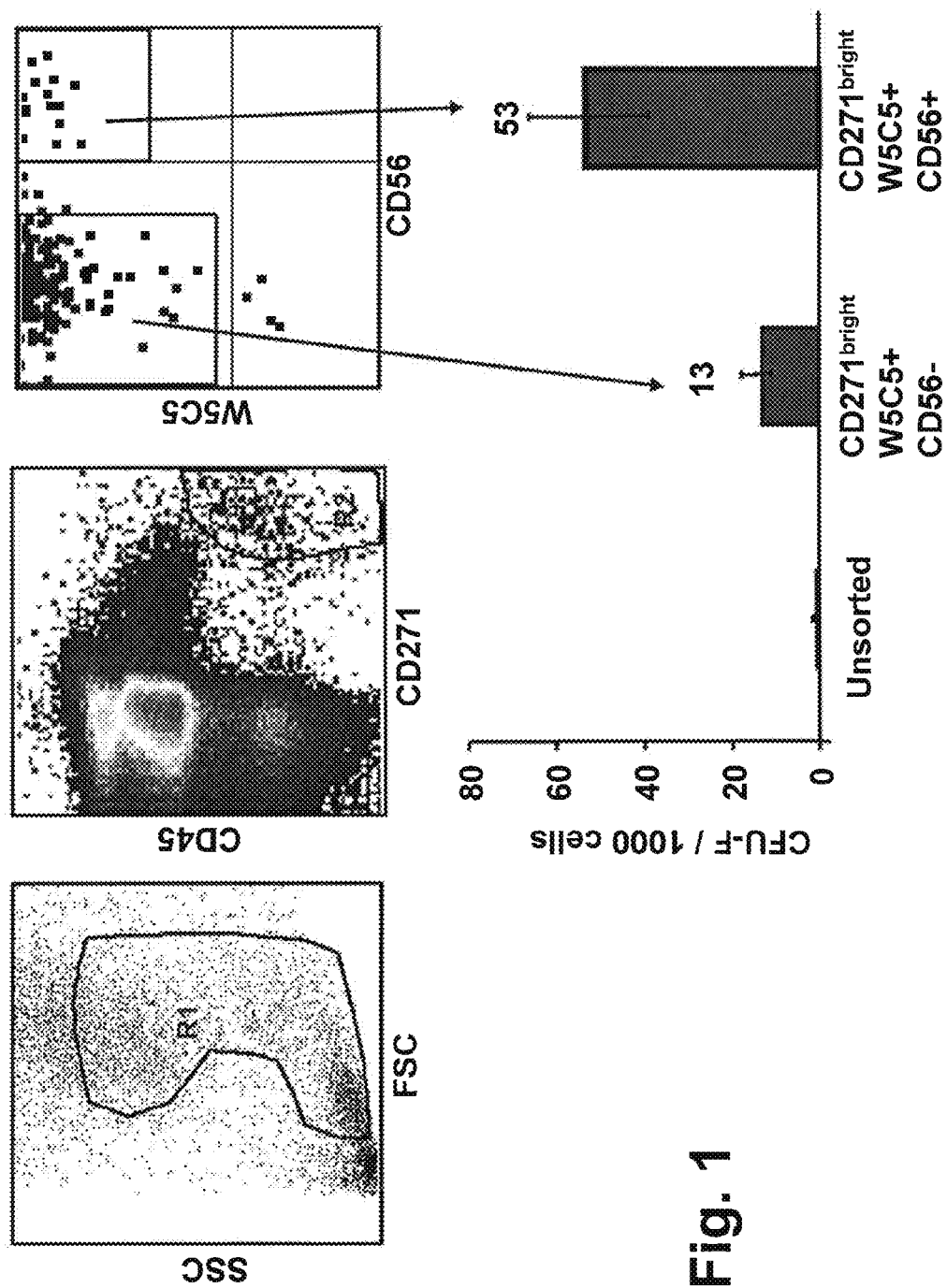
FIG. 1 shows CFU-F from SUSD2+(W5C5) bone marrow cells.
Figure 2A:
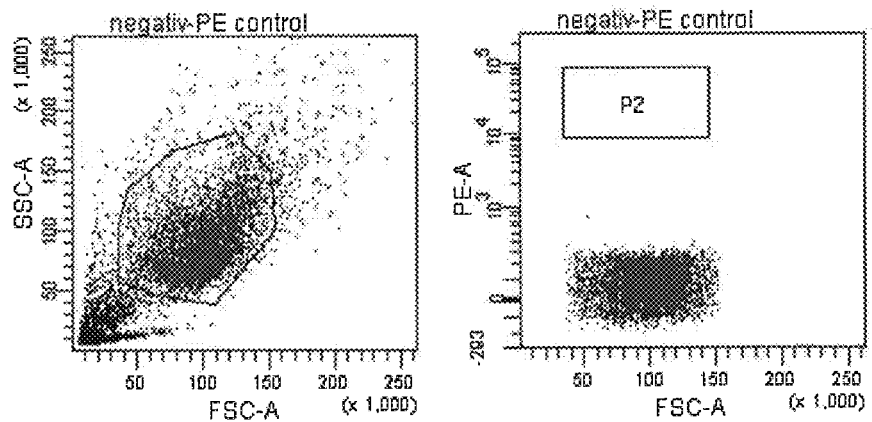
Figure 2B:
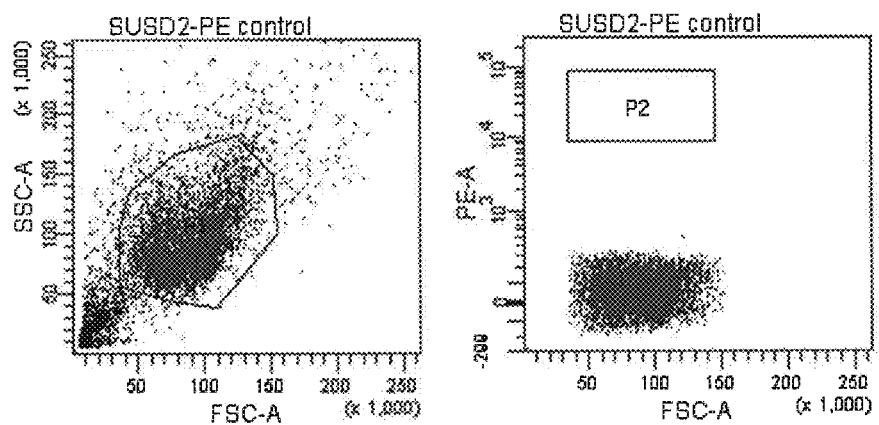
Figure 2C:
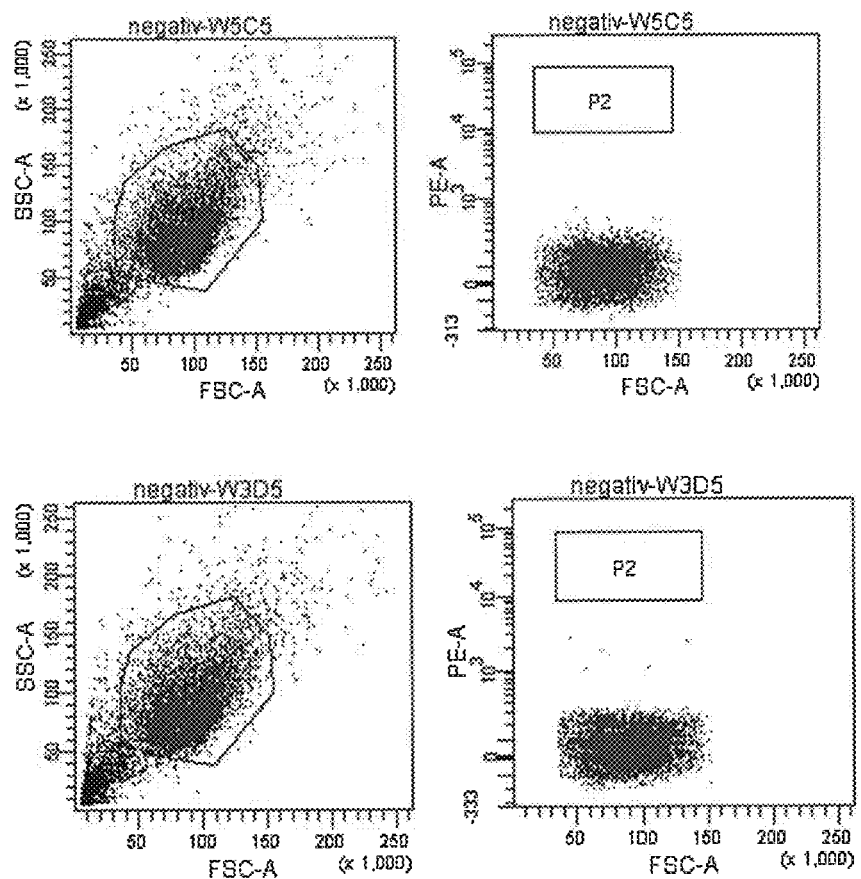
Figure 2D:
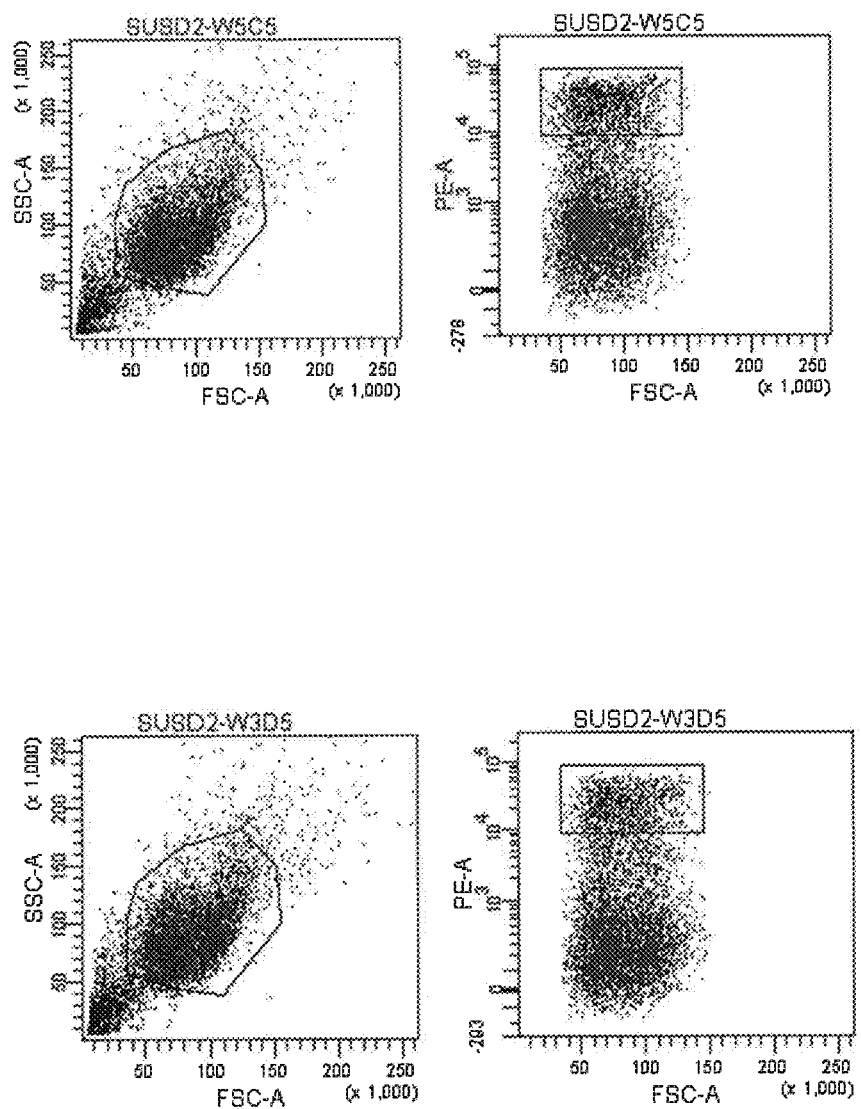

Bone marrow cells were labeled with CD271-APC, CD45 brilliant violet, CD56-FITC and W5C5-PE. A window was placed onto the CD271+CD45− MSC population and then in the plot resulting therefrom sorting windows were placed on the W5C5+cd56− and the W5C5+CD56+ populations. After the sorting, the colony forming number (CFU-F) capacity of the respective population was tested.

FIG. 2A-2D: SUSD2 identification:

The antibodies W5C5 and W3D5 recognize HEK-293 cells transfected with the SUSD2 gene: the FACS plots show both control stainings on both cell types (i.e. non-transfected HEK-293 cells (A) and SUSD2-transfected HEK-293 cells (B), and also specific stainings with the respective antibodies (non-transfected HEK-293 cells (C) and SUSD2-transfected HEK-293 cells (D)).

DESCRIPTION OF PREFERRED EMBODIMENTS

EXAMPLES

Material and Methods

Isolation and Cloning of Bone Marrow and Peripheral Blood Mononuclear Cells

After explanation and declaration of consent, bone marrow was obtained from the femoral shaft of patients at the Trade Association Clinic who had received an artificial hip joint after hip operations. Peripheral blood from healthy donors was obtained from the transfusion department of the Tubingen University Clinic. Mononuclear cells from the bone marrow and mononuclear cells from the blood were isolated by ficoll density gradient fractionation and the remaining erythrocytes lysed in an ammonium chloride solution.

Culturing of the Primary Cells

The ficoll-separated and FACS-enriched bone marrow cells were cultured as previously described: $2\times10^7$ unfractionated or $1\times10^4$ sorted MSCA-1+CD56+ and MSCA-1+CD56− BM cells were cultured in gelatin-coated T-75 or T-25 culture bottles, in the presence of 20 ml or 6 ml of Knockout™ replacement medium (Invitrogen, Karlsruhe, Germany) and 5 ng/ml of recombinant human fibroblast growth factor (rh-bFGF: CellSystems, Remagen, Germany). After culturing for three days, the non-adhering cells were removed and fresh medium added. The adhering cells were cultured until they reached 90% confluence.

Colony-Forming Fibroblast Assay (CFU-F)

CFU-F assays were performed by plating out either $1\times10^5$ unselected or 500-5,000 FACS-selected bone marrow cells into gelatin-coated T-25 bottles which contained Knockout™ medium and 5 ng/ml rh-bFGF. After culturing for twelve days, the adhering cells were washed twice with PBS, fixed for five minutes at room temperature with methanol (Sigma-Aldrich), air-dried and stained with Giemsa solution (Merck, Darmstadt, Germany). CFU-F colonies were counted macroscopically. The size of the colonies ranged from between 1 and 8 mm in diameter.

Immunofluorescence Analysis and Cell Sorting

Antibodies: the following antibodies were used: W5C5 (SUSD2), W3D5 (SUSD2), and W8B2 (TNAP), CD56-FITC (clone NCAM16.2) was purchased from Becton Dickinson (Heidelberg, Germany). The SSEA-4-reactive antibody MC-813-70 was obtained from Chemicon (Hampshire, Great Britain). CD271-APC and SUSD2-PE and SUSD2 coupled with beads were obtained from Miltenyi Biotec, Bergisch Gladbach.

Immunofluorescent staining: after blocking and specific bindings with 10 mg/ml polyglobin (10 mins, 4° C.), the cells were incubated for 15 mins with either 20 μl of antibodies or 10 μl of fluorochrome-conjugated antibodies. The cells stained with the conjugates were washed twice, suspended in 200 μl of FACS buffer and used for the flow cytometry. The cells which were labeled with the antibodies were stained for 15 mins with 20 μl of an $F(ab)_2$ fragment of the R-phycoerythrin (PE)-conjugated goat anti-mouse antibody (Dako Cytomations, Glostrup, Denmark), washed twice and analyzed by flow cytometry. For the multicolor staining, the cells were incubated for 15 mins with 10 μl of an anti-CD56-FITC, anti-TNAP-APC and anti-SUSD2-PE. After the washing, the cells were used for the flow cytometry. For combined indirect and direct staining, the cells were firstly labeled with the non-conjugated antibody and then stained for 15 mins with 20 μl of 1:25 diluted goat anti-mouse secondary antibody. The free binding sites of the secondary antibody were blocked by incubation of the cells for 25 mins with 20 μl of a mouse IgG polyclonal antibody (0.05 μg/ml; Southern Biotech, Birmingham, Ala.), before being counterstained with TNAP-APC and/or CD56-FITC. After a washing step, the cells were analyzed by flow cytometry.

Flow Cytometry Analyses and Cell Sorting

Bone marrow cells which had been labeled with anti-TNAP-APC, anti-SUSD2-PE and CD56-FITC were sorted with an FACSAria cell sorter (Becton Dickinson), by firstly placing a gate on the SUSD2 population and then setting the sorting windows in the resulting plot TNAP against CD56. The sorted cells were used for functional and phenotype analyses. The coexpression analyses were performed with an FACSCanto II flow cytometer (Becton Dickinson). The data were analyzed using the FCS Express software (De Novo Software, Ontario, Canada).

MACS Separation

In selected experiments, the bone marrow cells were presorted by MACS (Miltenyi Biotec) using SUSD2-PE and anti-PE MACS beads. The separations were performed in accordance with the manufacturer's instructions.

As already mentioned in the description of diagrams, in experiments bone marrow cells were labeled with CD271-APC, CD45-brilliant violet, CD56-FITC and W5C5-PE. Since MSC CD271 + are CD45+, a window was set on this population and then in the plot resulting therefrom sorting windows were set on the W5C5+CD56 +and W5C5+CD56− populations. After the sorting, the colony forming capacity of the respective populations was investigated (FIG. 1).

SUSD2 Identification

Cultured bone marrow MSC were simultaneously labeled with W3D5 and W5C5 and stained with a rabbit anti-mouse PE conjugate (by preliminary experiments with over 20 different cell types it was found that W5C5 and W3D5 had the same reactivity pattern). Next, the W5C5/W3D5− and W5C5/W3D5+++ cells were sorted in the FACS sorter and centrifuged down. The mRNA was isolated from the cell pellets (via Mltenyi, Germany) and a gene expression analysis of both fractions performed. It was found that in the W5C5/W3D5+++ fraction the SUSD2 gene was expressed higher by a factor of ca. 20 than in the W5C5/W3D5− fraction. Since there was no monoclonal SUSD2 antibody on the market, the complete sequence of the SUSD2 gene was acquired (Origen) and HEK-293 cells transfected therewith. 3 days after the transfection, the reactivity of W5C5 and W3D5 on the transfectants and the non-transfected HEK-293 cells was compared (FIG. 4). The FACS plots show both control stainings on both cell types (FIG. 4A, B) and also specific stainings with the respective antibodies (FIG. 4C, D). It was found that both antibodies selectively recognize the HEK293/huSUSD2 transfectants.

Thus with the present results it could be shown that the combination of at least the antibodies against SUSD2 and CD140b, TNAP and/or CD56 is suitable for isolating all MSC from bone marrow in high purity and very effectively, in particular since the two SUSD2 markers are highly selective for MSC. TNAP is strongly expressed on CD56− MSC but only weakly on CD56 +MSC. However, SUSD2 is equally strongly expressed on both subsets. The combination of both antibodies enables a more reliable selection of MSC owing to the signal reinforcement.

Hence with the present study a combination of antigens was identified, namely SUSD2 with CD104b, TNAP and/or CD56, via which MSC, in particular those with chondrogenic, adipocyte and osteogenic differentiation potential, can be effectively isolated and/or identified.

These results are particularly relevant with regard to the clinical use of such isolated stem cells and the chondrocytes, adipocytes and osteoblasts obtained via these stem cells. Thus for example injuries of articular cartilage and of vertebral disks are as a rule difficult to treat, precisely because of the limited regeneration potential of these tissues. Diseases such as rheumatoid arthritis, traumata, bone fractures and vertebral disk injuries are directly connected with the lack of effective chondrogenesis. In spite of the progress in orthopedics and increasing success in autologous chondrocyte transplantation, cell biology-based approaches for cartilage regeneration remain a challenge. The main problem is the use of cultured cells for clinical purposes in which the starting cells are only poorly characterized.

Hence the present invention offers the possibility for example of providing highly enriched and well defined MSC bone marrow cells with outstanding chondrogenic differentiation potential, which can be used as a starting population for clinical use. These cells can either be used directly for injection, for example into the vertebral disk spaces/vertebral disks, or proliferated in vitro and differentiated into chondrocytes before being used for clinical applications.

What is claimed is:

1. A method for the isolation and/or identification of mesenchymal stem cells with chondrocyte differentiation potential, the method comprising the following steps:
   a) contacting a sample which comprises mesenchymal stem cells with at least one antibody which binds to antigen SUSD2 (Sushi domain containing protein 2), or with an antigen binding fragment of the antibody,
   b) optionally contacting the sample with a further antibody which binds to the antigen SUSD2, or with an antigen binding fragment of the further antibody,
   c) contacting the sample with an antibody which binds to CD140b, an antibody which binds to CD56 and/or an antibody which binds to TNAP, or with an antigen binding fragment thereof, and/or
   d) identifying the cells in the sample which bind i) the at least one antibody which binds to the antigen SUSD2 or antigen-binding fragments thereof and ii) the at least one antibody or antigen binding fragment thereof which binds to CD140b, CD56 and/or TNAP,
   thereby isolating and/or identifying mesenchymal stem cells with chondrocyte differentiation potential.

2. The method as claimed in claim 1, wherein the antibody which binds to the antigen SUSD2, used in step a), is selected from the group consisting of:
   antibody W5C5 which is produced by the cell line deposited at the German Collection of Microorganisms and Cell Cultures with Accession No. ACC2813,
   antibody W3D5 which is produced by the cell line deposited at the German Collection of Microorganisms and Cell Cultures with Accession No. ACC2815,
   an antigen-binding fragment of antibody W5C5;
   an antigen binding fragment of antibody W3D5,
   an antibody which binds to the same epitope as the antibody W5C5; and
   an antibody which binds to the same epitope as antibody W3D5.

3. The method as claimed in claim 1, wherein the antibody which binds to CD140b used in step c) is selected from the group consisting of:
   antibody 28D4,
   an antigen binding fragment of antibody 28D4, and
   an antibody which bind to the same epitope as antibody 28D4.

4. The method as claimed in claim 1, wherein the antibody which binds to TNAP used in step c) is selected from the group consisting of:
   antibody W8B2 which is produced by the cell line deposited at the German Collection of Microorganisms and Cell Cultures with Accession No. ACC2567,
   an antigen binding fragment of antibody W8B2, and
   an antibody which bind to the same epitope as antibody W8B2.

5. The method as claimed in claim 1, wherein the antibody which binds to CD56 used in step c) is selected from the group consisting of:
   antibody 39D5, which is produced by the cell line deposited at the German Collection of Microorganisms and Cell Cultures with Accession No. ACC2930,
   an antigen binding fragments of antibody 39D5, and
   an antibody which bind to the same epitope as antibody 39D5.

6. The method as claimed in claim 1, wherein steps a), b) and c) are performed simultaneously, consecutively or in reverse order.

7. The method as claimed in claim 2, wherein the antibody W5C5 and/or W3D5, or antigen binding fragment thereof, are used in combination with the antibody which binds to CD104b, or an antigen binding fragment thereof.

8. The method as claimed in claim 2, wherein the antibody W5C5 and/or W3D5, or antigen binding fragment thereof, are used in combination with the antibody which binds to CD56, or an antigen binding fragment thereof.

9. The method as claimed in claim 2, wherein the antibody W5C5 and/or W3D5, or antigen binding fragment thereof, are used in combination with the antibody which binds to TNAP, or an antigen binding fragment thereof.

* * * * *